(12) United States Patent
Sievers

(10) Patent No.: US 7,758,638 B2
(45) Date of Patent: Jul. 20, 2010

(54) IMPLANT WITH AN ANNULAR BASE

(75) Inventor: Hans Hinrich Sievers, Kronshagen (DE)

(73) Assignee: ATS Medical, Inc., Plymouth, MN (US)

( * ) Notice: Subject to any disclaimer, the term of this patent is extended or adjusted under 35 U.S.C. 154(b) by 0 days.

(21) Appl. No.: 11/897,223

(22) Filed: Aug. 29, 2007

(65) Prior Publication Data

US 2008/0009941 A1    Jan. 10, 2008

Related U.S. Application Data

(63) Continuation of application No. 10/890,032, filed on Jul. 13, 2004, now Pat. No. 7,276,079.

(51) Int. Cl.
*A61F 2/24* (2006.01)
(52) U.S. Cl. .................................................. 623/2.36
(58) Field of Classification Search ....... 623/2.36–2.37; 606/213
See application file for complete search history.

(56) References Cited

U.S. PATENT DOCUMENTS

| | | | |
|---|---|---|---|
| 3,656,185 A | | 4/1972 | Carpentier |
| 4,055,861 A | | 11/1977 | Carpentier et al. |
| 4,164,046 A | | 8/1979 | Cooley |
| 5,061,277 A | | 10/1991 | Carpentier et al. |
| 5,104,407 A | | 4/1992 | Lam et al. |
| 5,171,252 A | * | 12/1992 | Friedland ............... 606/151 |
| 5,439,479 A | * | 8/1995 | Shichman et al. .......... 606/220 |
| 5,810,882 A | * | 9/1998 | Bolduc et al. ............. 606/213 |
| 6,183,512 B1 | * | 2/2001 | Howanec et al. ........... 623/2.36 |
| 6,231,602 B1 | | 5/2001 | Carpentier et al. |
| 6,726,717 B2 | | 4/2004 | Alfieri et al. |
| 6,805,710 B2 | * | 10/2004 | Bolling et al. ............. 623/2.36 |
| 6,858,039 B2 | | 2/2005 | McCarthy |
| 6,955,689 B2 | * | 10/2005 | Ryan et al. ............... 623/2.36 |
| 7,294,148 B2 | * | 11/2007 | McCarthy ................ 623/2.36 |
| 7,329,280 B2 | * | 2/2008 | Bolling et al. ............. 623/2.36 |
| 2002/0055773 A1 | | 5/2002 | Campbell et al. |
| 2003/0093148 A1 | | 5/2003 | Bolling et al. |
| 2003/0208264 A1 | | 11/2003 | McCarthy et al. |
| 2004/0006384 A1 | | 1/2004 | McCarthy |
| 2006/0129236 A1 | | 6/2006 | McCarthy |
| 2008/0058924 A1 | * | 3/2008 | Ingle et al. ................ 623/2.36 |
| 2008/0154359 A1 | * | 6/2008 | Salgo et al. ................ 623/2.36 |

FOREIGN PATENT DOCUMENTS

DE    694 03 482    12/1997

(Continued)

OTHER PUBLICATIONS

German Priority Application Search Report.

*Primary Examiner*—Suzette J Gherbi
(74) *Attorney, Agent, or Firm*—Haugen Law Firm PLLP

(57) ABSTRACT

The implant has an annularly bent base, whereby the imagined surface enclosed by the base is bent. Preferably the surface enclosed by the base is a symmetrical. It is particularly advantageous if the base is enclosed by a solid material and this is enclosed by a relatively soft material. This offers the possibility of designing fastening clips in the relatively solid material. Such implants are especially suited as heart valve rings.

1 Claim, 2 Drawing Sheets

FOREIGN PATENT DOCUMENTS

Figure 1:
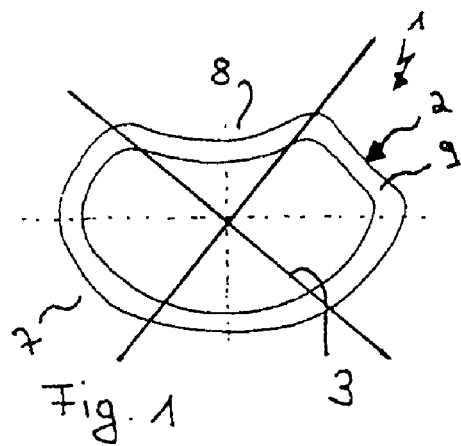

| | | |
|---|---|---|
| DE | 690 33 195 | 3/2000 |
| EP | 1 034 753 | 9/2000 |
| EP | 1 258 232 | 11/2002 |
| EP | 1 348 406 | 10/2003 |
| WO | WO 97/16135 | 5/1997 |
| WO | WO 99/49817 | 10/1999 |
| WO | WO 00/62715 | 10/2000 |
| WO | WO 03/053289 | 7/2003 |

* cited by examiner

IMPLANT WITH AN ANNULAR BASE

CROSS REFERENCE TO RELATED APPLICATIONS

This application is a continuation and claims priority under 35 U.S.C. §120 of U.S. patent application Ser. No. 10/890,032 filed Jul. 13, 2004 now U.S. Pat. No. 7,276,079.

The invention relates to an implant with an annular base.

Implants with annular bases are used in different parts of the body. Examples of these in particular are inlets and outlets of vessels, synthetic intestinal outlets and the like. The invention relates in particular to stabilizing rings for a heart valve annulus.

The object of heart valves in human or animal hearts, depending on state of contraction, is to permit blood flow in the open state or to prevent reflux in the closed state. This function is regulated by the heart valves flaps, which close precisely in the closed state of the valves. The overall geometry of heart valves ensures that the flaps lie precisely above one another to prevent reflux.

Various heart conditions can lead to deforming of the heart valves annuli. This can result in deforming of the whole valve geometry. And the result of this is that the valve flaps no longer lie on one another precisely and the function of the heart valve is restricted thereby. This is frequently accompanied by leakage through the closed heart valve or worsening of the valve dynamic and thus delay in the closing phase. The performance of the heart thereby deteriorates substantially.

Valves damaged in this way can be replaced by synthetic heart valve prostheses. The prostheses adequately fulfil the function of the damaged valve; however this method does have certain limitations due to the restricted fatigue strength or extraneous materials used.

A view-rich alternative to synthetic heart valve prosthesis is represented by surgical correction of the valve annulus. Here a more or less flexible ring is attached in the valve annulus, which should restore the physiological geometry.

These methods are based on inventions by Carpentier (U.S. Pat. No. 3,656,185) and Cooley (U.S. Pat. No. 4,164,046) and are clinically established.

The rings used are however in many cases not optimally suited both as rigid and as flexible rings to cause simply shaping of the valve annulus, which ensures tight closing of the valve flaps.

The object of the invention is therefore to further develop an implant with an annular base, such that it adapts optimally to as many applications as possible.

This task is solved by an implant with an annular base, in which the imagined surface enclosed by the base is bent inwards in a first quadrant and is first bent inwards and then outwards in a subsequent second quadrant.

The inventive implant has an annular base, which is designed such that the imagined surface enclosed by the base is bent according to particular preset values. This enables it to produce rings, which are adapted optimally to the physiological conditions and also remain in the mechanically unstressed state in this form. Depending on the case a wide range of forms of ring can be made, which are either adapted individually to the diseased vessel outlet, or depending on size and flexion can be prefabricated and marketed for different uses.

It is advantageous if the imagined surface enclosed by the base is bent outwards in a third and in a fourth quadrant. It has eventuated that for medical applications a concave peripheral line lying approximately fully in the first quadrant is an advantage. On one side convex peripheral lines connect thereto via the following two quadrants, and the fourth quadrant is approximately half convex and in the other half configured flattened or even concave.

For clinical application it is particularly advantageous if the imagined surface enclosed by the base is bent in on itself.

Known implant rings exhibit a bi-dimensional geometry. In part these rings can also be deformed in the third dimension. For this the rings are designed elastic. However, this results in the ring again assuming a bi-dimensional structure in the non-mechanically stressed state. The bent-in form of the base leads to the implant being delivered with a preset shape, which must no longer be adapted during an operation, or only slightly so.

An advantageous embodiment provides that in cross-section the imagined surface enclosed by the base has a point of inflexion. Viewed from the side such a base has concave and convex regions and depending on usage there can even be several points of inflexion. This allows optimal ring shapes to be produced, which both in plan view and in side elevation deviate from simple geometric basic shapes. The imagined surface enclosed by the base thus has at least a saddle shape or an S-shaped bend in a section line.

It has eventuated that the form of the ring does not necessarily have to be a circular shape. It is advantageous if the imagined surface enclosed by the base is asymmetrical. In particular, annular bases, which are constructed neither point- nor mirror-symmetric, enable optimal adaptation to the annulus geometry to be found in the body. This is especially significant for implants in the region of the heart valve annulus.

A rise in adaptability—but possibly also a drop in durability—is achieved by the base being plastically deformable. This enables the base to be formed subsequently just prior to an operation, so that it can best adapt to the present physiological conditions.

A material, which can be made plastically ductile by physical or chemical treatment for a specific period, is particularly preferred. This enables the ring to be formed optimally prior to implantation, whereby afterwards and in particular in the implanted situation the ring is no longer ductile or is only still elastically ductile. This material can for example be made plastically ductile by heat treatment. As the material cools down to body temperature below 42° C., it loses its plastic ductility.

In addition synthetics with memory effect can also be used. Such synthetic materials can be deformed in any way. But as long as they are brought to a temperature range of the human body temperature, they assume a previously defined form.

Above all for the use of annular bases for strengthening the heart valve annulus is it an advantage if the imagined surface enclosed by the base has at least one concave bent edge region. In the event of heart valve annulus treatment this concave bent edge region is arranged advantageously between the Trigoni Fibrosae.

An embodiment provides that the base is enclosed by a multilayer material, preferably a tissue. This embodiment is advantageously independent of the previously described ring geometries and essential to the invention. When the known implants with annular bases are used this can lead to problems in anchoring to the surrounding tissue, such as for example of the heart on account of considerable stress from the high load exchange. Known implants have a metallic ring, which is enclosed by a seam ring. Here the problem arises that this can lead to the structure of the seam ring coming away from the metallic core. Also it can result in destruction of the structure and to individual fibres being torn out from the localised strain of the seam ring.

This is combated according to the present invention by the base being enclosed by a multilayer tissue. Preferably the base is enclosed by a solid material and this is enclosed by a relatively soft material. This results in at least one three-ply situation of base material, the solid material enclosing the base and the relatively soft material enclosing this material.

In this case the base is preferably formed from a metallic material. As mentioned hereinabove however different synthetic materials can also be used.

The multilayer structure enables a core material to be used, which contributes substantially to shaping. The superposed first layer establishes a solid connection to the core material and comprises a relatively solid material. The second layer comes into contact with the surrounding tissue in the implanted state and has the usual soft character. In fixing the ring the seam can be guided through the second layer as usual. For solid anchoring the seam however can also be guided through the inner, solid material. This ensures for example a substantially improved fixing of a valve ring also at high localised stresses.

Another embodiment provides that the base has puncture channels. The implant can be fastened to the surrounding tissue either by sewing onto tissue enclosing the base, or the base consists of a softer material, which can be penetrated by the needle. It is particularly advantageous however if already prefabricated channels are arranged in the base puncture, which can serve to anchor the threads during implantation.

Depending on the application is it suggested that the puncture channels are designed round or oval in plan view.

In order to find the puncture channels more easily and to thread the needle through the puncture channels, it is proposed that the puncture channels have funnel-shaped openings. The puncture channels are thus widened in the edge region. This enlarges the opening, whereas in the middle region a smaller puncture channel opening guarantees the stability of the implant.

An advantageous embodiment provides that the puncture channels are arranged in the middle of the base cross-section. Hereby the stability of the implant is restricted the least. Depending on use it is also advantageous to arrange the puncture channels offset to the centre of the base cross-section, preferably relocated outwards. The seam is laid in the outer region of the implant. Depending on surgical premises various position of the seam can be established relative to the implant body. By way of example the puncture channel can also be arranged offset to the imagined surface enclosed by the base.

Depending on use the puncture channels enable tissue enclosing the base to be dispensed with even completely. The puncture channels however can also guarantee different fastening options for the implant during the operation in combination with tissue enclosing the base.

It is also advantageous if the implant has a fastening clip. Such a fastening clip is also advantageous and essential to the invention independently of the geometry and the layer structure of the implant. A fastening clip enlarges the geometric region, in which the thread can be fixed during implantation. An embodiment provides that the fastening clip is arranged in a material enclosing the base. Since the base is usually a metallic material, arranging the fastening clip in a material enclosing the base enables the implant to be made particularly simply.

Here the material enclosing the base, in which the fastening clip is designed, can be a solid material.

Solid material within the framework of the description of the invention is understood as a material, which allows a thread to be drawn through this material with a needle to connect the material with the tissue enclosing the implant. On the other hand however the solid material should have a greater strength than known tissue materials, which are used for anchoring metallic bases in the body by sewing.

The fastening clip or several fastening clips can be provided on the particularly stressed regions of the implant to guarantee secure anchoring. Implantation however is made easier by the fastening clip enclosing the base annularly. This enables the implant to be anchored on the entire peripheral line not only with the softer tissue material, but also enables the seam to be guided through the fastening clip made of a preferably more solid material.

In particular for processing a preformed heart valve annulus it is an advantage if the implant has at least one reinforced fixing point. This feature of the inventive implant is also essential to the invention without the previously described features. Preferably fixing points are arranged on two sides of a concave bent edge region. With strengthening of a heart valve annulus these fixing points are designed such that the stress can be input centrally to the valve ring. The position of the fixing points is in this case selected advantageously such that it allows fixing to the Trigoni Fibrosae in keeping with the anatomical conditions.

Advantageous embodiments of an inventive implant are illustrated in the diagram and are explained in greater detail hereinbelow.

Figure 2:
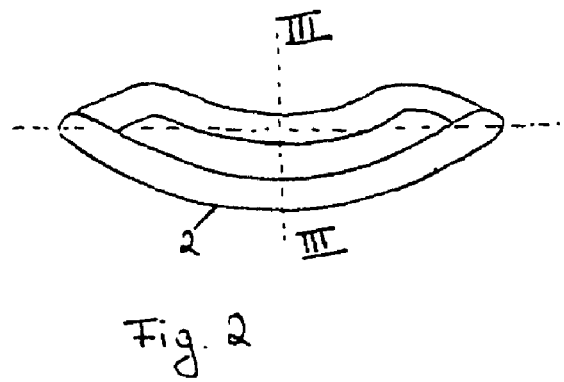
Figure 3:
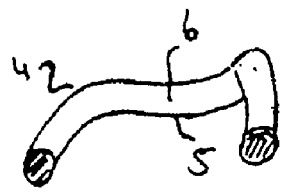
Figure 4:
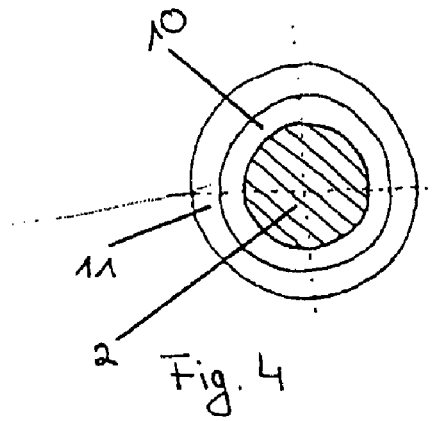
Figure 5:
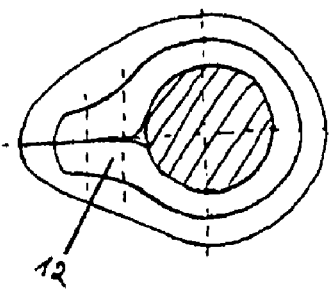
Figure 6:
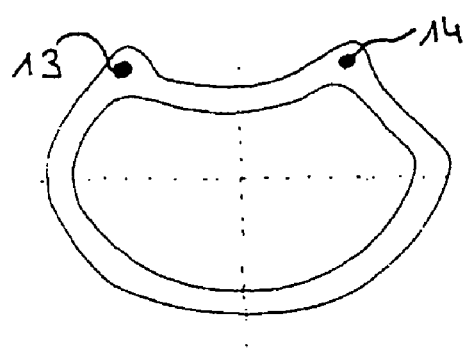
Figure 7:
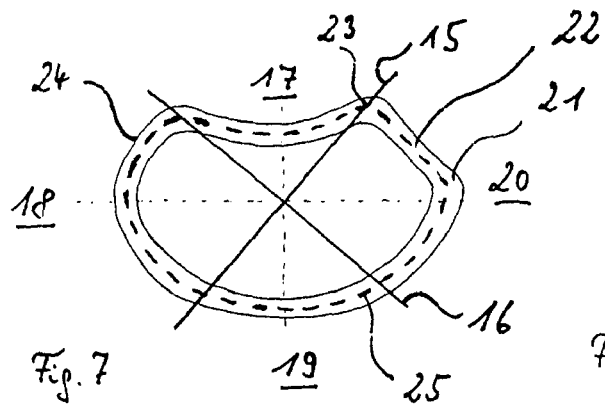
Figure 8:
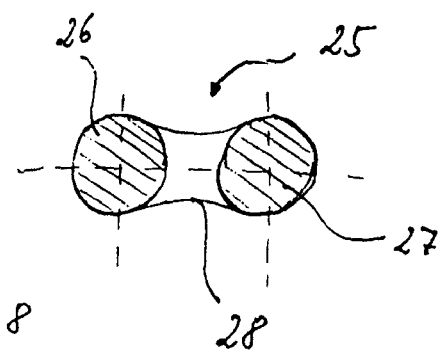
Figure 9:
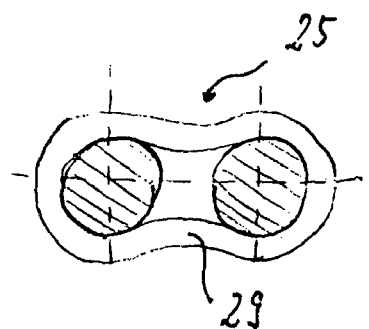
Figure 10:
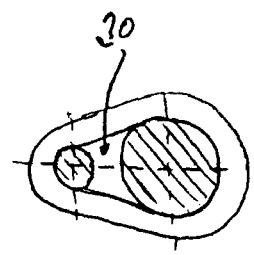
Figure 11:
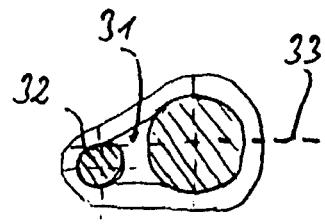
Figure 12:
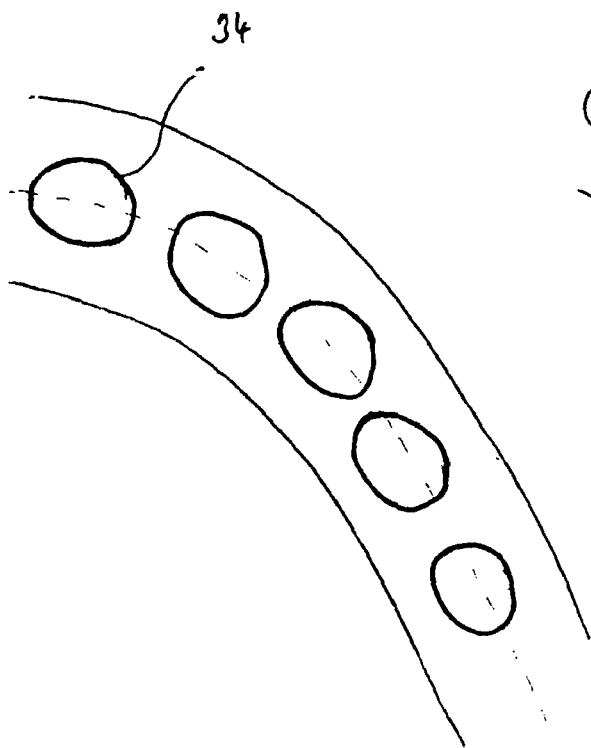
Figure 13:
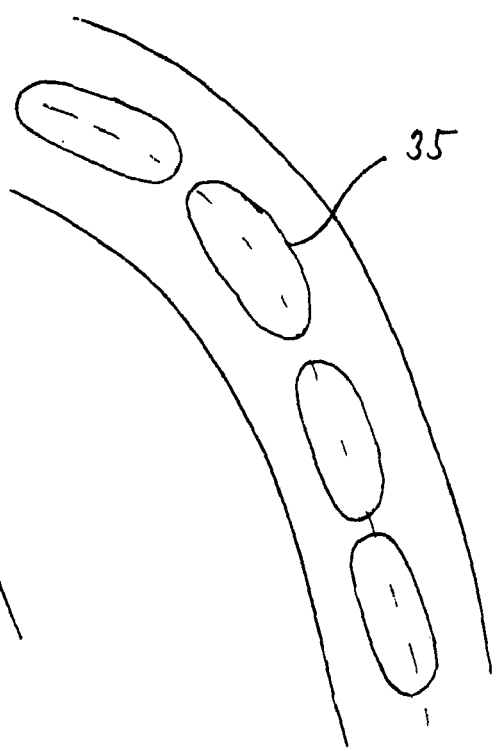

FIG. 1 is a plan view of an annular implant,

FIG. 2 is a side elevation viewed from the front of the annular implant shown in FIG. 1, FIG. 3 is a side elevation viewed from the side of the annular implant shown in FIG. 1, FIG. 4 is a section through an annular region of the implant shown in FIG. 1, FIG. 5 is a section through an annular region of the implant shown in FIG. 1 in the region of a fastening clip, FIG. 6 is a plan view of an implant corresponding to the implant shown in FIG. 1, though with two fixing points, FIG. 7 is a plan view of an implant with drawn-in quadrant and puncture channels, FIG. 8 is a section through the implant shown in FIG. 7, FIG. 9 is a view of the section shown in FIG. 8 with enclosing tissue, FIG. 10 is an alternative embodiment in section through the implant with decentralized puncture channels, FIG. 11 is another embodiment in section with a puncture channel, which is arranged offset to the imagined surface enclosed by the base, FIG. 12 is an enlarged view of a section of a base with round puncture channels, and FIG. 13 is an enlarged view of a section of a base with oval designed puncture channels.

The implant 1 shown in FIG. 1 has an annular base 2, which encloses an imagined surface 3. The side elevations shown in FIGS. 2 and 3 explain that the imagined surface 3 has a bent form. In the present case it is bent in an S-shape. It therefore has opposite bent regions 4 and 5, between which a point of inflexion 6 lies.

In particular FIG. 1 shows that the imagined surface enclosed by the base is asymmetrical. The region 7 of the base 2 has approximately the form of an ellipse, while the remaining peripheral region in the region 8 is bent opposite and in the region 9 is designed approximately straight.

FIG. 4 shows that the base 2 is enclosed by two material layers 10 and 11. In this embodiment the base comprises a metallic core material. This is enclosed by a relatively solid material 10. The relatively solid material 10 creates a good connection to the metallic core material 2 and is enclosed by the second layer 11. In the implanted state the second layer 11 comes into contact with the enclosing tissue and has the usual soft characteristic. When the ring is being fixed this enables the seam to be guided through the inner rigid tissue 10 to ensure particularly good fixing of a valve ring with high localised stresses also.

FIG. 5 shows that the implant 1 can also have a fastening clip 12. This fastening clip 12 is formed in the embodiment by the second layer 10 made of relatively solid material. Because the fastening clip 12 is designed such the geometrical region, in which the thread can be fixed, is enlarged. The fastening clip 12 can enclose the entire base annularly.

FIG. 6 shows an implant with two fixing points 13 and 14. These fixing points 13 and 14 lie to the right and left of a concave bent edge region of the annular base. These fixing points are designed such that the stress can be input centrally into a valve ring. The position of the fixing points is adapted to the anatomical conditions and should allow fixing to the Trigoni Fibrosae.

In FIG. 7 an implant is divided into four quadrants by means of the lines 15 and 16 lying orthogonally to one another. In the first quadrant 17 the edge line of the implant is bent inwards and is thus concave, whereas the edge line of the implant is bent outwards in both the other quadrants 18 and 19 attaching thereto on the left. In the fourth quadrant 20 the edge line of the implant is first bent outwards, as in the quadrant lying in front, and a bend 21 is provided approximately in the centre of the fourth quadrant, which leads through to a flattened or slightly inwardly bent partial region 22. This partial region 22 goes as far as another bend 23, which lies approximately at the transition from the fourth quadrant to the first quadrant. Provided in the base 24 of the implant are lengthy puncture channels 25, of which a large number is arranged on the base 24 of the implant.

The section shown in FIG. 8 shows a possible embodiment of such puncture channels 25. The channel 25 divides the base 24 in the region of the puncture channels into two base cross-sectional areas 26, 27 circular in cross-section. A funnel-shaped structure 28, which facilitates a needle being inserted into the puncture channel 25, is created due to the structuring of the base in the transition region to the puncture channel.

The puncture channels enable an embodiment without tissue enclosing the base. Yet also with use of tissue enclosing the base—as shown in FIG. 9—the channel 25 facilitates the anchoring of threads on the base, as long as the threads are guided through the enclosing tissue 29 and the puncture channel 25.

FIGS. 10 and 11 show that the puncture channels do not have to be arranged in the centre of the base. Slight offsetting of the puncture channels 30 radially outwards, as shown in FIG. 10, enables the implant to be sewn into its radial outer region. FIG. 11 shows a puncture channel 31, in which the outer part 32 of the base is arranged offset to the imagined surface 33 enclosed by the base. This facilitates the implant to be sewn onto the surrounding tissue.

Also, with the funnel-shaped design of the access to the puncture channel the puncture channels, as shown in FIGS. 12 and 13, can be designed as round openings 34 or as oval openings 35. The oval openings 35 extend in a longitudinal direction of the base so as to impair the stability of the base minimally only.

Another description of the implant provides that the base in the plan view is designed bean-shaped with a flattened side. The complex interplay enclosing the base of concave and convex lines corresponds substantially to the outer contour of a bean, whereby a flattened surface or another shorter surface bent inwards is provided attached to the inwards bent surface.

The embodiments show implants, which are designed for use as a valve ring. Implants according to the present invention can however be used for different applications in surgery and in particular for strengthening outlets and vessels.

The invention claimed is:

1. An implant comprising:
   (a) a base;
   (b) a solid material annularly enclosing the base, an outer surface of said solid material defining a solid material perimeter, said solid material having a fastening clip, in which a thread can be fixed during implantation, said fastening clip defining an enlarged geometrical region of said solid material wherein said solid material perimeter is spaced from said base to a substantially greater extent than a second spacing between said base and said solid material perimeter at all remaining regions of said solid material; and
   (c) a second material layer disposed about said outer surface of said solid material.

* * * * *